(12) United States Patent
Nakatani (10) Patent No.: US 9,518,969 B2
(45) Date of Patent: Dec. 13, 2016

(54) GAS ANALYSIS APPARATUS

(75) Inventor: Shigeru Nakatani, Kyoto (JP)

(73) Assignee: Horiba, Ltd., Kyoto (JP)

( * ) Notice: Subject to any disclaimer, the term of this patent is extended or adjusted under 35 U.S.C. 154(b) by 109 days.

(21) Appl. No.: 14/351,494

(22) PCT Filed: Sep. 3, 2012

(86) PCT No.: PCT/JP2012/072382
§ 371 (c)(1),
(2), (4) Date: May 20, 2014

(87) PCT Pub. No.: WO2013/054609
PCT Pub. Date: Apr. 18, 2013

(65) Prior Publication Data
US 2014/0301899 A1    Oct. 9, 2014

(30) Foreign Application Priority Data
Oct. 12, 2011    (JP) .................................. 2011-225294

(51) Int. Cl.
*G01N 33/62* (2006.01)
*G01N 33/00* (2006.01)
*G01N 1/22* (2006.01)

(52) U.S. Cl.
CPC ...... *G01N 33/0009* (2013.01); *G01N 33/0054* (2013.01); *F01N 2560/021* (2013.01);
(Continued)

(58) Field of Classification Search
CPC ............ G01N 33/0009; G01N 33/0054; G01N 33/0024; G01N 1/2252; F01N 2560/021; F01N 2610/02
See application file for complete search history.

(56) References Cited

U.S. PATENT DOCUMENTS

2007/0044457 A1*   3/2007   Upadhyay ............... F01N 3/208
                                                               60/295
2010/0047144 A1    2/2010   Hammer et al.
(Continued)

FOREIGN PATENT DOCUMENTS

CN           101513592 A        8/2009
CN           102165154 A        8/2011
(Continued)

OTHER PUBLICATIONS

EESR dated Aug. 18, 2015 issued for European patent application No. 12 840 684.0, 10 pgs.
(Continued)

*Primary Examiner* — Lyle Alexander
*Assistant Examiner* — Robert Eom
(74) *Attorney, Agent, or Firm* — Brooks Kushman P.C.

(57) ABSTRACT

In order to completely decompose remaining urea contained in exhaust gas emitted from an internal combustion engine to make it possible to accurately measure an amount of the remaining urea, as well as preventing measurement accuracy and reliability from being damaged by some cause such as the attachment of powdery urea on a sensor, a gas analysis apparatus is provided with a filter part that is provided between a sampling port and a produced substance measuring mechanism in a mixed gas sampling pipe to collect urea in a solid state or in a state of being dissolved in water in mixed gas.

7 Claims, 6 Drawing Sheets

(52) U.S. Cl.
CPC ........ *F01N 2610/02* (2013.01); *G01N 1/2252* (2013.01); *G01N 33/0024* (2013.01)

(56) References Cited

U.S. PATENT DOCUMENTS

| | | |
|---|---|---|
| 2011/0167801 A1 | 7/2011 | Massner |
| 2011/0252771 A1 | 10/2011 | Fujinaga et al. |

FOREIGN PATENT DOCUMENTS

| | | |
|---|---|---|
| EP | 2325452 A1 | 5/2011 |
| EP | 2357331 A1 | 8/2011 |
| GB | 2449162 A | 11/2008 |
| JP | 2002155733 A | 5/2002 |
| JP | 2010514545 A | 6/2010 |
| JP | 2010223650 A | 10/2010 |
| WO | 2010034403 A1 | 4/2010 |

OTHER PUBLICATIONS

Office Action dated Jul. 3, 2015 issued for Chinese Patent Application No. 201280049668.4, 8 pgs.

International Search Report for PCT/JP2012/072382, English translation attached to original, Both completed by the Japanese Patent Office on Dec. 11, 2012, 5 Pages.

* cited by examiner

FIG. 6

GAS ANALYSIS APPARATUS

CROSS-REFERENCE TO RELATED APPLICATIONS

This application is the National Stage of International Application No. PCT/JP2012/072382, filed Sep. 3, 2012, which claims priority to Japanese Patent Application No. 2011-225294, filed Oct. 12, 2011, the disclosures of each of which are incorporated in their entirety by reference herein.

TECHNICAL FIELD

The present invention relates to a gas analysis apparatus that measures a substance contained in exhaust gas emitted from an internal combustion engine or mixed gas in which the exhaust gas is mixed.

BACKGROUND ART

In the past, a gas analysis apparatus has been used to measure a composition of exhaust gas emitted from an internal combustion engine of an automobile, such as $NO_X$, and in recent years, a composition such as ammonia has also been measured.

As specific examples of measuring the gas composition such as ammonia, which has not been measured in the past, include a scene of research and development of a urea SCR (Selective Catalytic Reduction) system that can highly efficiently drive a diesel engine and also suppress a production amount of $NO_X$, and other scenes. To specifically describe the urea SCR system, the urea SCR system is configured to, by spraying urea into high-temperature exhaust gas emitted from a diesel engine, and as a reducing agent, supplying ammonia produced by pyrolysis of the urea to an SCR catalyst, reduce $NO_X$ in the exhaust gas to change the $NO_X$ to harmless $N_2$ and $H_2O$.

In the case where in such a urea SCR system, an excessive amount of urea is supplied, ammonia is contained in an exhaust gas emitted from a muffler or the like to give rise to a bad odor, or to failure to meet environmental standards. For this reason, in order to know whether or not an adequate amount of urea can be supplied in various driving conditions, ammonia in exhaust gas is measured.

Figure 6:
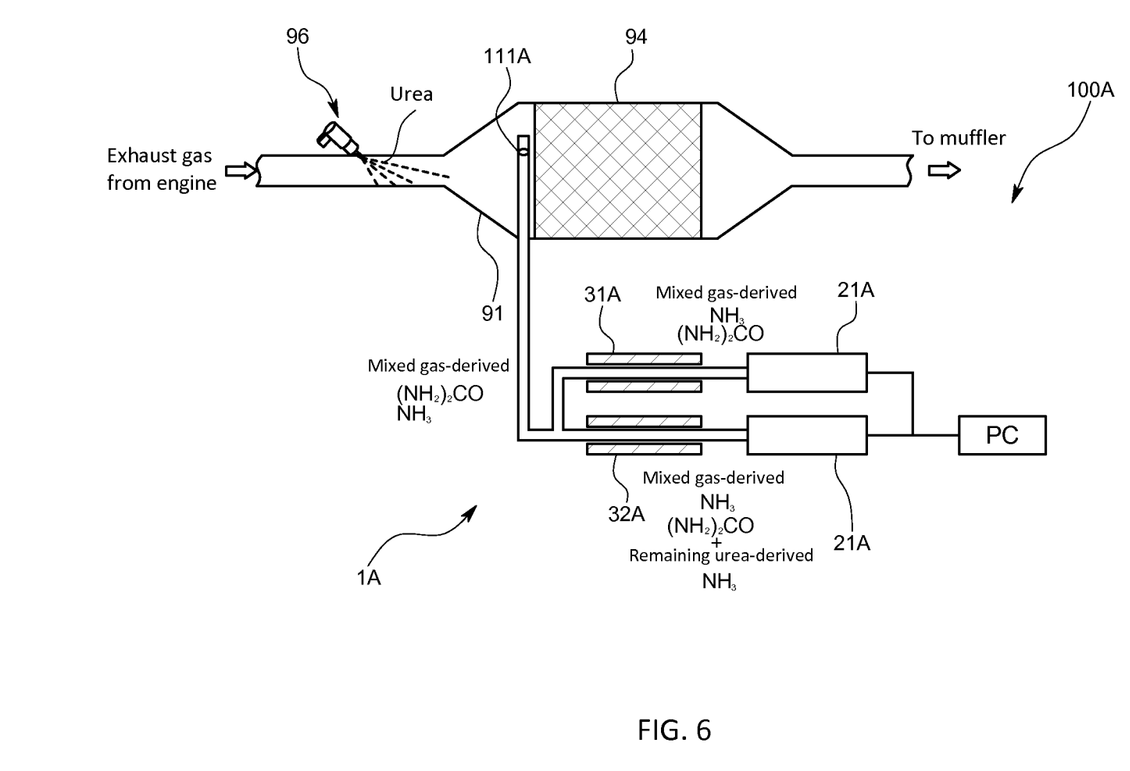
FIG. 6 is a schematic diagram illustrating a conventional gas analysis apparatus.

For example, JP-A2010-223650 discloses a gas analysis apparatus 100A that measures an amount of urea remaining in exhaust gas only with ammonia sensors 21A that can measure the concentration of ammonia. More specifically, as illustrated in FIG. 6, the analysis apparatus 100A is one provided with: a sampling pipe 1A of which one end is opened just before an SCR catalyst 94 and the other ends (of sampling pipe branches) are provided with the ammonia sensors 21A; and heaters 31A and 32A that are respectively provided so as to surround the sampling pipe branches 1A on upstream sides of the ammonia sensors 21A. Also, the gas analysis apparatus 100A is configured to measure first concentration of ammonia while heating the inside of one of the sampling pipe branches 1A with the heater 31A so as to keep the urea contained in the exhaust gas at a temperature lower than a pyrolysis starting temperature of the urea, and second concentration of ammonia while heating the inside of the other sampling pipe branch 1A with the heater 32A to temperature higher than the pyrolysis starting temperature of the urea, and from a difference between the concentrations, calculate an amount of the remaining urea contained in the exhaust gas.

In addition, it is expected that isocyanic acid, which may be produced in the case of introducing urea into the exhaust gas for the urea SCR, also becomes increasingly important in measurement in future because an influence of isocyanic acid on an environment, health, and the like is quantitatively evaluated. Further, JP-A2010-223650 also describes a method for calculating an amount of isocyanic acid produced from urea by a decomposition reaction.

Meanwhile, even in the gas analysis apparatus as disclosed in JP-A2010-223650, it is required to further improve measurement accuracy and reliability of the remaining urea and isocyanic acid in the exhaust gas.

Specifically, in order to accurately measure an amount of the remaining urea in the exhaust gas, it is necessary to completely decompose the remaining urea into the ammonia in the sampling pipe, and obtain an accurate amount of the ammonia derived from the remaining urea. However, at present, there is a possibility that sufficiently heating and completely decomposing urea in a misty state or powdery urea resulting from extracting water are not sufficiently performed.

On the other hand, in the case of measuring the amount of the isocyanic acid produced from the urea by heat of the exhaust gas, if even part of the remaining urea is pyrolyzed in the sampling pipe, in addition to the isocyanic acid produced by the heat of the exhaust gas in the first place, isocyanic acid newly produced in the sampling pipe is included. That is, the evaluation may be made on the basis of a more excessive amount than the amount of the isocyanic acid emitted from an actual vehicle.

In other words, even in any of the measurement of the urea and the measurement of the isocyanic acid produced from the urea, in order to increase accuracy and reliability, it is necessary to appropriately control the decomposition reaction of the remaining urea contained in mixed gas.

Also, in the case where the powdery urea arrives at each of the ammonia sensors without being decomposed, there exists another problem that the urea is attached on a surface of a sensor part, or the like to reduce sensitivity and reduce reliability of a measured value, and consequently calculated values of the urea and isocyanic acid amounts may become unreliable.

SUMMARY OF INVENTION

Technical Problem

The present invention is made with the intention to solve the problems as described above at once, and intended to provide a gas analysis apparatus that is adapted to be able to, in the case of calculating a remaining urea amount, completely decompose remaining urea contained in exhaust gas emitted from an internal combustion engine to accurately measure the remaining urea amount, and in the case of calculating an isocyanic acid amount, calculate an accurate value with preventing urea from being newly decomposed at the time of measurement, as well as preventing measurement accuracy and reliability from being damaged due to the attachment of powdery urea on a sensor or another cause.

Solution to Problem

That is, the gas analysis apparatus of the present invention is provided with: a mixed gas sampling pipe that, from a sampling port formed on one end side, samples mixed gas that is a mixture of exhaust gas emitted from an internal combustion engine and a misty urea aqueous solution; a decomposition reaction controlling mechanism that controls a decomposition reaction of urea or isocyanic acid in the mixed gas sampling pipe; a produced substance measuring mechanism that is provided on the other end side of the mixed gas sampling pipe and measures a value related to an amount of a substance produced from the urea or the isocyanic acid in the urea aqueous solution; a calculation part that, on a basis of a measured value measured by the produced substance measuring mechanism, calculates a urea amount calculated value that is a value related to an amount of the urea contained in the mixed gas; and a filter part that is provided between the sampling port and the produced substance measuring mechanism in the mixed gas sampling pipe to collect the urea in a solid state or in a state of being dissolved in water in the mixed gas, wherein the decomposition reaction controlling mechanism is configured to act on the filter part.

Also, the gas analysis apparatus of the present invention is provided with: a mixed gas sampling pipe that, from a sampling port formed on one end side, samples mixed gas that is a mixture of exhaust gas emitted from an internal combustion engine and a misty urea aqueous solution; a decomposition reaction controlling mechanism that controls a decomposition reaction of urea or isocyanic acid in the mixed gas sampling pipe; a produced substance measuring mechanism that is provided on the other end side of the mixed gas sampling pipe and measures a value related to an amount of a substance produced from the urea or the isocyanic acid in the urea aqueous solution; a calculation part that, on a basis of a measured value measured by the produced substance measuring mechanism, calculates an isocyanic acid amount calculated value that is a value related to an amount of the isocyanic acid contained in the mixed gas; and a filter part that is provided between the sampling port and the produced substance measuring mechanism in the mixed gas sampling pipe to collect the urea in a solid state or in a state of being dissolved in water in the mixed gas, wherein the decomposition reaction controlling mechanism is configured to act on a downstream side of the filter part.

If so, between the sampling port and the produced substance measuring mechanism, the filter part is provided, and therefore the urea in the solid state such as a powdery state or in the state of being dissolved in water is collected by the filter part. Accordingly, in the case where the decomposition reaction controlling mechanism acts so as to start the decomposition reaction of the urea, the urea can be completely decomposed to then measure an amount of a urea-derived substance without arriving at the produced substance measuring mechanism as the urea is before the complete end of the decomposition. Further, the calculation part can calculate the urea amount calculated value on the basis of an accurate amount of the urea-derived substance produced by the decomposition of substantially the whole of the urea contained in the exhaust gas, and therefore accurately calculate an amount of the remaining urea contained in the exhaust gas. On the other hand, in the case where the decomposition reaction controlling mechanism does not start the decomposition reaction of the urea, the urea in the solid state or in the state of being dissolved in water, which are contained in the exhaust gas, is prevented by the filter part from arriving at the produced substance measuring mechanism, and therefore a situation such as a reduction in reliability of a measured value due to a reduction in sensitivity caused by, for example, the attachment of the urea on a sensing part or the like of a sensor can be prevented. From another point of view, the filter part collects the urea in the solid state or in the state of being dissolved in water, and therefore the decomposition reaction controlling mechanism can selectively perform a decomposition reaction of only the isocyanic acid without applying heat to the urea in such a state to cause pyrolysis. Accordingly, measurement targeting only the isocyanic acid contained in the mixed gas can be performed to improve measurement accuracy of the isocyanic acid as well.

As described, the gas analysis apparatus is provided with the filter part, so that accuracy of a measured value of a substance produced from the urea or isocyanic acid, or accuracy of the calculated value of the urea or isocyanic acid amount can be increased to increase reliability of the measured value or calculated value.

As a specific aspect for controlling the decomposition reaction of the urea in the exhaust gas, it is only necessary that the decomposition reaction controlling mechanism is configured to control temperature of the filter part, and the calculation part is configured to calculate the urea amount calculated value that is a value related to an amount of the urea contained in the mixed gas.

Specific aspects of a measuring target and temperature setting for accurately calculating the amount of the urea contained in the mixed gas by the calculation part include an aspect in which: the produced substance measuring mechanism is configured to measure a value related to an amount of ammonia; the decomposition reaction controlling mechanism is configured to be able to control the temperature of the filter part to a first temperature that is equal to or more than a temperature at which water is evaporated and less than a pyrolysis starting temperature that is a temperature at which production of ammonia and isocyanic acid is started by a pyrolysis reaction of urea, or a second temperature that is equal to or more than the pyrolysis starting temperature and less than a hydrolysis starting temperature that is a temperature at which production of ammonia is started by a hydrolysis reaction of isocyanic acid; and the calculation part is configured to calculate the urea amount calculated value on a basis of a first ammonia measured value measured at the first temperature by the produced substance measuring mechanism and a second ammonia measured value measured at the second temperature by the produced substance measuring mechanism.

Other aspects for measuring an amount of a substance other than ammonia to thereby calculate the amount of the urea contained in the mixed gas include an aspect in which: the produced substance measuring mechanism is configured to measure a value related to an amount of isocyanic acid; the decomposition controlling mechanism is configured to be able to control the temperature of the filter part to a first temperature that is equal to or more than a temperature at which water is evaporated and less than a pyrolysis starting temperature that is a temperature at which production of ammonia and isocyanic acid is started by a pyrolysis reaction of urea, or a second temperature that is equal to or more than the pyrolysis starting temperature and less than a hydrolysis starting temperature that is a temperature at which production of ammonia is started by a hydrolysis reaction of isocyanic acid; and the calculation part is configured to calculate the urea amount calculated value on a basis of a first isocyanic acid measured value measured at the first temperature by the produced substance measuring mechanism and a second isocyanic acid measured value measured at the second temperature by the produced substance measuring mechanism.

In order to make it possible to accurately measure each of an amount of a urea-derived substance produced in such a way that the urea is decomposed by heat of the exhaust gas emitted from the internal combustion engine and an amount of a urea-derived substance produced in such a way that the urea, which is not decomposed by the heat of the exhaust gas but remains, is decomposed by the decomposition reaction controlling mechanism, it is only necessary that the first temperature is less than 133° C., and the second temperature is equal to or more than 133° C. and less than 160° C. Setting such temperatures makes it possible to, at the first temperature, without causing the decomposition reaction of the urea, in the sampling pipe, keep amounts of ammonia and isocyanic acid originally present in the exhaust gas, and at the second temperature, produce equal parts of ammonia and isocyanic acid on the basis of the decomposition reaction of the urea contained in the exhaust gas. Also, at the second temperature, a hydrolysis reaction of the isocyanic acid can be substantially prevented from being caused, and therefore a production ratio of the ammonia with respect to the urea can be kept substantially constant to increase calculation accuracy of the urea amount calculated value. Preferably, it is cited that the first temperature is set equal to or more than 40° C. and equal to or less than 128° C., and the second temperature is set equal to or more than 138° C. and equal to or less than 155° C. Setting such temperature zones makes it possible to prevent moisture from condensing on a pipe or the like, and also absorb unevenness and deviation of temperature control by the decomposition reaction controlling mechanism to further increase measurement accuracy.

In order for the calculation part to be able to use a simple operation to accurately calculate an amount of the isocyanic acid by preventing a decomposition reaction from the urea contained in the mixed gas from being newly caused, it is only necessary that the decomposition reaction controlling mechanism is configured to control temperature of the inside of the mixed gas sampling pipe on a downstream side of the filter part, and the calculation part is configured to calculate the isocyanic acid amount calculated that is the value related to the amount of the isocyanic acid contained in the mixed gas.

In order for the calculation part to be able to use a simple operation to calculate the amount of the isocyanic acid by not directly measuring the isocyanic acid contained in the mixed gas but performing measurement of a more easily measurable substance, it is only necessary that the produced substance measuring mechanism is configured to measure a value related to an amount of ammonia; the decomposition reaction controlling mechanism is configured to be able to control the temperature of the filter part to a first temperature that is equal to or more than a temperature at which water is evaporated and less than a pyrolysis starting temperature that is a temperature at which production of ammonia and isocyanic acid is started by a pyrolysis reaction of urea, or a third temperature that is equal to or more than a hydrolysis starting temperature that is a temperature at which production of ammonia is started by a hydrolysis reaction of isocyanic acid; and the calculation part is configured to calculate the isocyanic acid amount calculated value on a basis of a first ammonia measured value measured at the first temperature by the produced substance measuring mechanism and a third ammonia measured value measured at the third temperature by the produced substance measuring mechanism.

In order for the calculation part to be able to accurately calculate the amount of the isocyanic acid contained in the mixed gas in such a simple way that the produced substance measuring mechanism measures only ammonia, it is only necessary that the first temperature is less than 133° C., and the third temperature is equal to or more than 160° C. In order to take into account an error or the like of temperature control to increase reliability of a measured value, it is preferable to set the third temperature to 165° C. or more.

Advantageous Effects of Invention

As described, according to the gas analysis apparatus of the present invention, the filter part is provided between the sampling port of the sampling pipe and the produced substance measuring mechanism, and therefore misty or powdery undecomposed urea from remaining urea contained in the exhaust gas emitted from the internal combustion engine can be collected before arriving at the produced substance measuring mechanism. Further, the collected remaining urea can be completely decomposed in the filter part, and substantially the whole of the remaining urea can be completely measured in the produced substance measuring mechanism in a state of being decomposed. Accordingly, the remaining urea that has been unmeasurable in the past because of passing through the produced substance measuring mechanism as a state of urea can also be accurately measured to accurately calculate a remaining urea amount. Also, the remaining urea is collected in the filter part, and therefore can be separated from the isocyanic acid contained in the mixed gas, and only the isocyanic acid can be measured without pyrolyzing the urea, so that the amount of the isocyanic acid contained in the mixed gas can also be accurately calculated. Further, the misty or powdery urea can be collected in the filter part and prevented from arriving at the produced substance measuring mechanism, and therefore measurement accuracy and reliability can be prevented from being damaged by some cause such as the attachment of the powdery urea on a sensor.

REFERENCE SIGNS LIST

100 Gas analysis apparatus
1 Mixed gas sampling pipe
111 Sampling port
21 Ammonia sensor (produced substance measuring mechanism)
22 Fourier transform infrared spectroscopic analyzed (produced substance measuring mechanism)
3 Decomposition reaction controlling mechanism
4 Filter part
5 Calculation part

DESCRIPTION OF EMBODIMENTS

A first embodiment of the present invention is described with reference to drawings.

A gas analysis apparatus 100 of the present embodiment is one that is intended to measure an amount of urea remaining in gas emitted from a vehicle mounted with a urea SCR system 200. The vehicle is one that is mounted with a diesel engine as an internal combustion engine 92, and the urea SCR system 200 is formed in an exhaust pipe 91 connected to the diesel engine.

Figure 1:
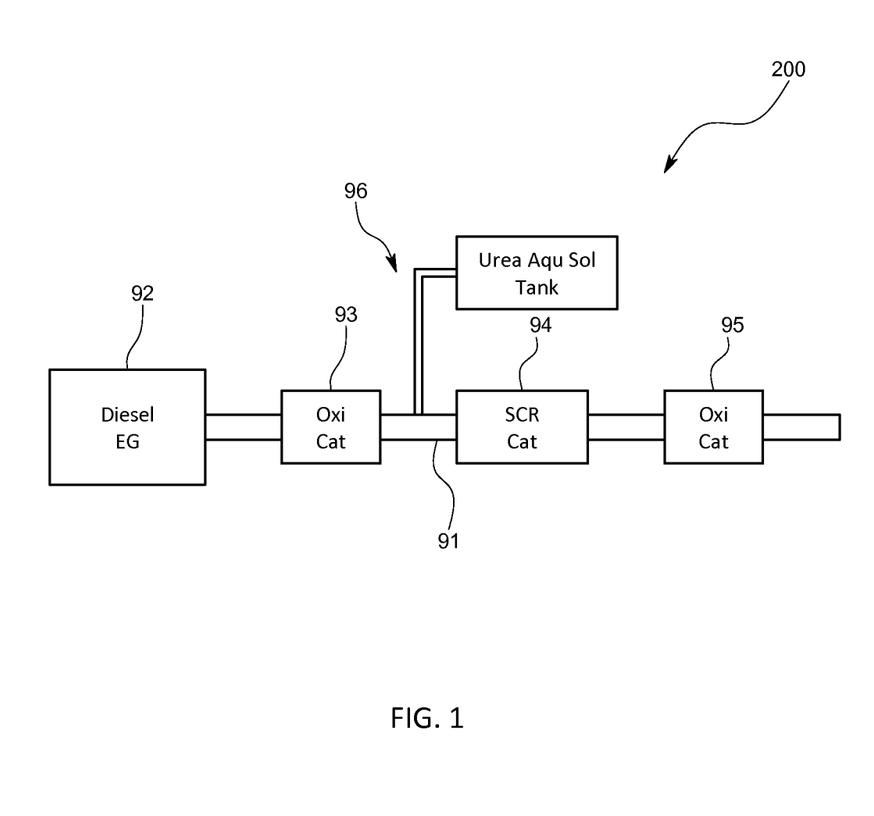
FIG. 1 is a conceptual diagram of a urea SCR system.

The urea SCT system 200 is, as illustrated in FIG. 1, configured to include, sequentially from an upstream side in the exhaust pipe 91, a first oxidation catalyst 93, a urea injecting mechanism 96 that injects urea into the exhaust pipe 91, an SCR catalyst 94, and a second oxidation catalyst 95, and ammonia produced by the decomposition of the urea injected from the urea injecting mechanism 96, and the SCR catalyst 94 cooperate to thereby reduce NO and $NO_2$ having passed through the first oxidation catalyst 93 to nitrogen and water.

More specifically, in the urea SCR system 200, the urea injecting mechanism 96 is one that brings a 32.5% urea aqueous solution, which is prepared by dissolving urea in water, into a mist state to inject the misty urea aqueous solution into the exhaust pipe 91, and adapted to facilitate pyrolysis of urea. That is, between the urea injecting mechanism 96 and the SCR catalyst 94, the exhaust gas emitted from the internal combustion engine 92 and the misty urea aqueous solution are mixed with each other and brought into a mixed gas state.

Note that if an amount of the urea injected from the urea injecting mechanism 96 is excessive, and ammonia having an amount more than an amount necessary to reduce NO and $NO_2$ is produced, ammonia not consumed at the time of reducing NO and $NO_2$ may be contained in gas emitted from the vehicle to fail to meet environmental standards. Also, it is necessary to grasp what ratio of the urea injected from the urea injecting mechanism 96 is decomposed by heat of the exhaust gas to produce the ammonia, and control the amount of the urea to be injected to an appropriate value depending on a driving condition or the like.

The gas analysis apparatus 100 of the present embodiment is, in order to solve the problem as described above in the urea SCR system 200, configured to measure a remaining urea amount between the urea injecting mechanism 96 and the SCR catalyst 94.

Figure 2:
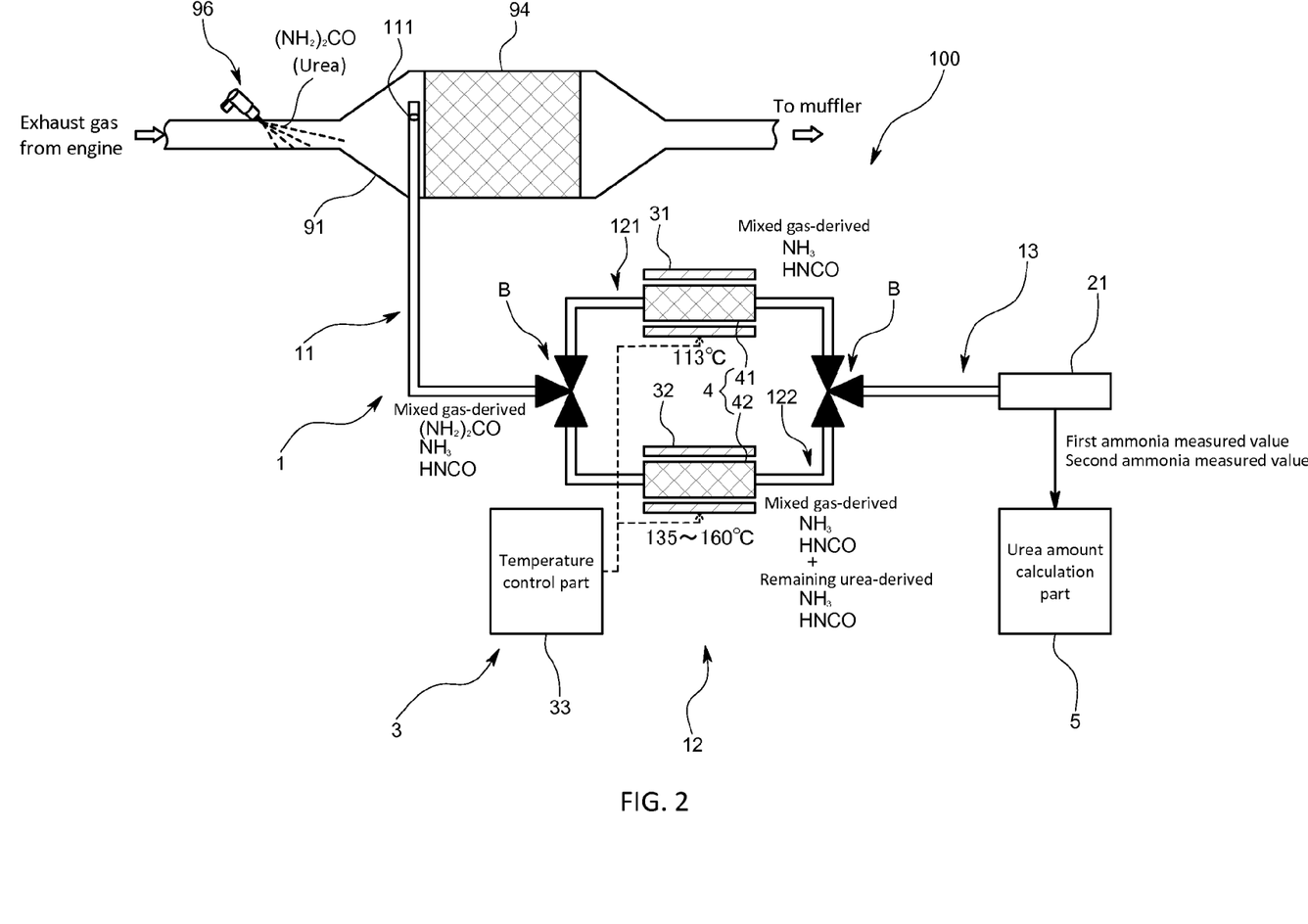
FIG. 2 is a schematic diagram illustrating a gas analysis apparatus according to a first embodiment of the present invention.

More specifically, the gas analysis apparatus 100 is one that is, as illustrated in FIG. 2, provided with: a mixed gas sampling pipe 1 that is formed with a sampling port 111 between the urea injecting mechanism 96 and the SCR catalyst 94 in the exhaust pipe 91 to sample mixed gas containing the exhaust gas and the urea aqueous solution; a filter part 4 that is provided in the mixed gas sampling pipe 1 to collect urea in a solid state or in a state of being dissolved in water in the mixed gas; a decomposition reaction controlling mechanism 3 that controls a decomposition reaction of the urea in the mixed gas sampling pipe 1; a produced substance measuring mechanism that is provided on the other end side of the mixed gas sampling pipe 1 and measures a value related to an amount of a substance produced from the urea in the urea aqueous solution; and a calculation part 5 that, on the basis of the measured value measured by the produced substance measuring mechanism, calculates a urea amount calculated value that is a value related to an amount of the urea contained in the mixed gas.

In addition, in the gas analysis apparatus 100 of the first embodiment, the decomposition reaction controlling mechanism 3 is one that controls temperature inside the sampling pipe 1 to thereby control the decomposition reaction of the urea, and the produced substance measuring mechanism is an ammonia sensor 21 for measuring ammonia produced by the decomposition of urea. Also, the calculation part 5 is configured to, on the basis of ammonia amounts measured by the ammonia sensor 21, calculate the amount of the urea that remains without being decomposed by the heat of the exhaust gas in the exhaust pipe 91.

The respective parts are further described in detail.

The mixed gas sampling pipe 1 is configured to include: an introduction part 11 that forms from the sampling port 111 to a branching point; a branching part 12 that, from the branching point, branches into two flow paths, which again meet together as one path at a meeting point; and a terminal part 13 that forms a pipe from the branching point to the produced substance measuring mechanism. The introduction part 11 is adapted to flow the exhaust gas introduced from the exhaust pipe 91 in an unchanged state. The branching part 12 is provided with a first flow path 121 and a second flow path 122, and the filter part 4 is provided for the flow paths. Further, the present embodiment is configured such that the after-mentioned decomposition reaction controlling mechanism 3 switches directional control valves B respectively provided at the branching and meeting points to thereby flow the mixed gas through any one of the flow paths and also make a urea decomposition condition different. The mixed gas having passed through the first or second flow path 121 or 122 moves through the terminal part 13 and arrives at the ammonia sensor 21.

The filter part 4 includes first and second filters 41 and 42 respectively provided in the first and second flow paths 121 and 122 in the branching part 12, and each of the filters is a glass fiber filter for collecting a solid substance or a liquid substance contained in the mixed gas. In particular, the glass fiber filter in the present embodiment is formed as a filter having density that makes it possible to collect the misty urea aqueous solution or solid powdery urea formed by evaporation of water as a solvent of the urea aqueous solution, which is contained in the mixed gas.

The decomposition reaction controlling mechanism 3 is configured to include: first and second heaters 31 and 32 that are respectively provided on outer sides of the first and second flow paths 121 and 122; and a temperature control part 33 that separately controls temperatures inside the first and second flow paths 121 and 122 with the first and second heaters 31 and 32. The temperature control part 33 is, together with the calculation part 5, configured to fulfill its function by a so-called computer provided with a CPU, memory, A/D and D/A converters, and input/output interface.

The temperature control part 33 is configured to, in a state where the directional control valves B are switched such that the mixed gas flows only through the first flow path 121, use the first heater 31 to control temperature inside the first flow path 121, in particular, temperature near the first filter 41 to a first temperature that is equal to or more than a temperature at which water is evaporated, and less than a pyrolysis starting temperature that is a temperature at which the production of ammonia and isocyanic acid is started by the pyrolysis reaction of urea. More specifically, the first temperature is set less than 133° C. Considering an effect of preventing condensation on the pipe, and unevenness and deviation of temperature control, the first temperature is preferably set to 40° C. or more and 128° C. or less. That is, in the case where the mixed gas flows through the first flow path 121, the present embodiment is adapted to, in the exhaust pipe 91, keep an amount of the ammonia produced by the decomposition of the urea, and regulates temperature to keep the temperature at 113° C. so as to prevent the remaining urea from being pyrolyzed.

Further, the temperature control part 33 is adapted to, in a state where the directional control valves B are switched such that the mixed gas flows only through the second flow path 122, use the second heater 32 to control temperature near the second filter 42 to a second temperature that is equal to or more than the pyrolysis starting temperature and less than a hydrolysis starting temperature that is a temperature at which the production of ammonia is started by a hydrolysis reaction of isocyanic acid. More specifically, the second temperature is set to be equal to or more than 133° C. and less than 160° C. In order to consider unevenness and deviation of temperature control to provide a more reliable measured value, the second temperature is also preferably set equal to or more than 138° C. and equal to or less than 155° C. In the present embodiment, the temperature control part 33 performs the temperature control to keep the inside of the second flow path 122 equal to or more than 135° C. and less than 160° C. so as to surely start the pyrolysis of the urea. By setting the temperature to such a second temperature, in the second flow path 122, in particular, near the second filter 42, the following pyrolysis reaction is caused because the temperature is higher than 133° C.

$$(NH_2)_2CO \rightarrow NH_3 + NH=C=O \quad \text{(chemical formula 1)}$$

Here, $(NH_2)_2CO$ is urea, and $NH=C=O$ is isocyanic acid.

In addition, in the presence of water at 160° C. or more, the hydrolysis reaction as expressed by a chemical formula 2 is caused in the isocyanic acid.

$$NH=C=O + H_2O \rightarrow NH_3 + CO_2 \quad \text{(chemical formula 2)}$$

Accordingly, rewriting the above chemical formulae as a urea-based chemical formula leads to the following chemical formula.

$$(NH_2)_2CO + H_2O \rightarrow 2NH_3 + CO_2 \quad \text{(chemical formula 3)}$$

That is, depending on how to set the second temperature, it is determined that with respect to urea, ammonia is produced on a one-to-one basis as expressed by the chemical formula 1, or in a one-to-two basis as expressed by the chemical formula 3. As will be described later, the present embodiment is adapted to produce ammonia constantly on the one-to-one basis with respect to urea by setting the second temperature to the hydrolysis reaction temperature or less so as to decrease a calculation error at the time of calculating the remaining urea amount from measured amounts of ammonia.

Further, apart from the chemical formulae described above, by heating urea, biuret or cyanuric acid may be produced to change a yield of ammonia. To describe this more specifically, in the case of heating urea at a temperature higher than 133° C., crystallized biuret and gaseous ammonia are produced as expressed by the following chemical formula 4.

$$2(NH_2)_2CO \rightarrow H_2N-CO-NH-CO-NH_2 + NH_3 \quad \text{(chemical formula 4)}$$

Here, $H_2N-CO-NH-CO-NH_2$ is biuret.

Further, in the case of heating biuret at a temperature higher than 188° C., solid cyanuric acid and ammonia are produced from the biuret as expressed by the following chemical formula 5.

$$3H_2N-CO-NH-CO-NH_2 \rightarrow 2C_3H_3N_3O_3 + 3NH_3 \quad \text{(chemical formula 5)}$$

Here, $C_3H_3N_3O_3$ is cyanuric acid.

In the present embodiment, the second temperature is set to a temperature lower than 188° C. at which cyanuric acid is produced, and therefore a relationship in production amount between the remaining urea and the newly produced ammonia can be kept at approximately one to one. Accordingly, the calculation part 5 can calculate an accurate value at the time of calculating the remaining urea amount.

The ammonia sensor 21 as the produced substance measuring mechanism is a sensor of which a sensing part formed of zirconia, which has responsiveness only to ammonia, and for example, even in the case where isocyanic acid arrives at the ammonia sensor 21, an output is not provided as a measured value. Also, the ammonia sensor 21 is configured to output the concentration of ammonia contained in the mixed gas.

The calculation part 5 is configured to, on the basis of a first ammonia measured value that is ammonia concentration measured in a state where the mixed gas is flowed through the first flow path 121 and kept at the first temperature in the first flow path 121, and a second ammonia measured value that is ammonia concentration measured in a state where the mixed gas is flowed through the second flow path 122 and kept at the second temperature in the second flow path 122, calculate a urea amount calculated value that is the amount of the remaining urea not decomposed in the exhaust pipe 91. More specifically, the calculation part 5 calculates the urea amount calculated value on the basis that from the above-described chemical formula 1, a difference between the second ammonia measured value and the first ammonia measured value corresponds to an amount of ammonia produced by pyrolysis of the remaining urea. For example, the calculation part 5 is adapted to calculate a molar number of the ammonia on the basis of the difference between the second ammonia measured value and the first ammonia measured value, and on the assumption that urea having an equivalent molar number remains on the basis of the chemical formula 1, output the urea amount calculated value.

As described, according to the gas analysis apparatus 100 of the first embodiment, the powdery or misty urea remaining in the mixed gas can be collected by the first and second filters 41 and 42 respectively provided in the first and second flow paths 121 and 122. Accordingly, a measurement error caused on the basis that the remaining urea arrives at the ammonia sensor 21 without being decomposed and the urea cannot be fully decomposed can be substantially eliminated. Also, a reduction in sensitivity due to the attachment of a solid substance such as the powdery urea on the ammonia sensor 21 can be prevented.

Further, the decomposition reaction controlling mechanism 3 performs the temperature control so as to cause only the pyrolysis of the urea expressed by the chemical formula 1, and therefore an error can be prevented from occurring in the estimation of the remaining urea amount due to, for example, the creation of another reaction system for cyanuric acid, biuret, or the like associated with the hydrolysis reaction, or the like.

From these, it can be verified with an exact value whether or not the amount of the urea injected into the exhaust pipe 91 from the urea injecting mechanism 96 in the urea SCR system 200 has an adequate value, and therefore the gas analysis apparatus 100 having high reliability can be configured.

Next, a second embodiment of the present invention is described. In the following description, members corresponding to those described in the first embodiment are denoted by the same reference signs.

Figure 3:
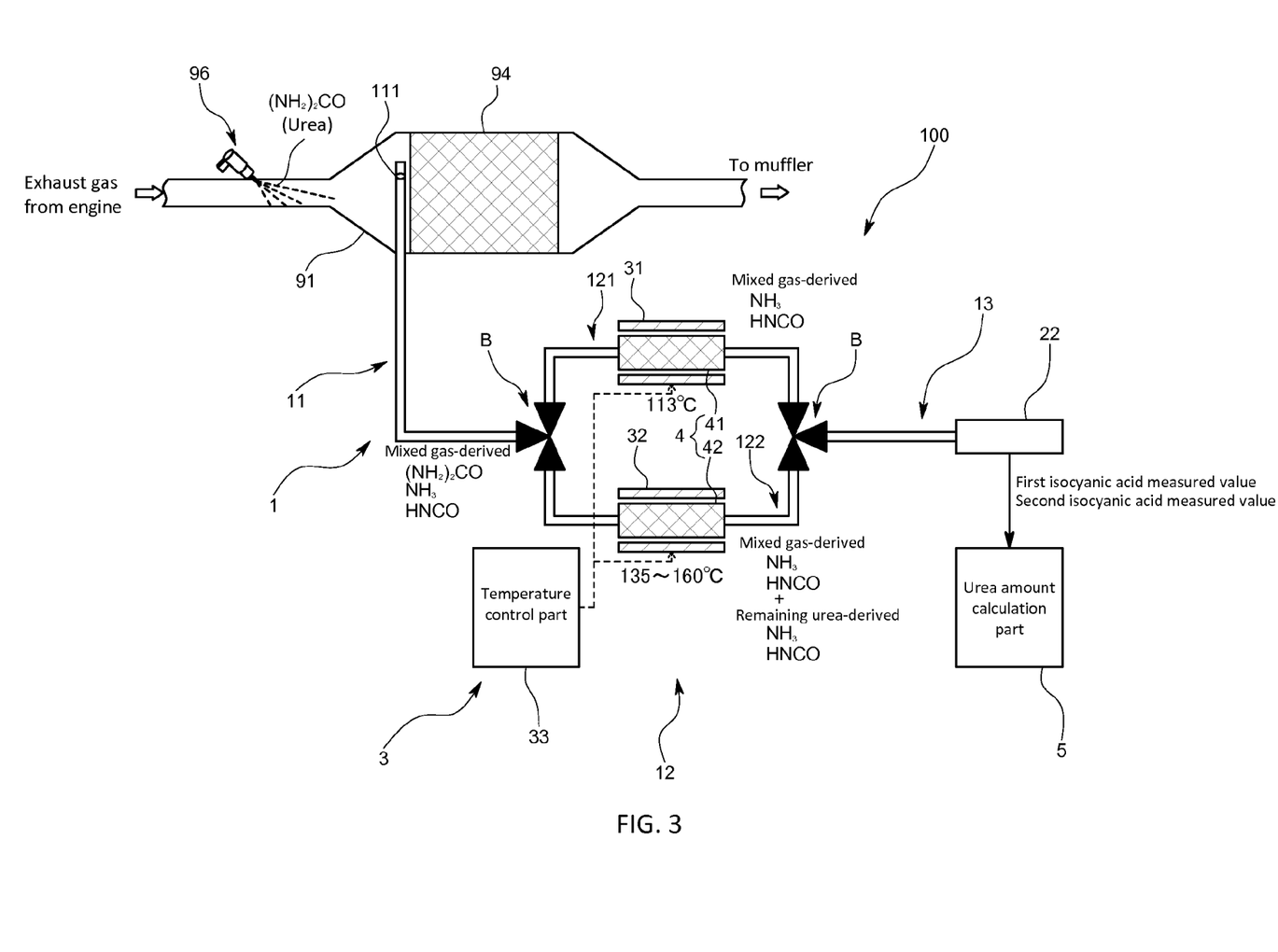
FIG. 3 is a schematic diagram illustrating a gas analysis apparatus according to a second embodiment of the present invention.

A gas analysis apparatus 100 of the second embodiment is configured not to measure ammonia but, as illustrated in FIG. 3, to measure isocyanic acid to thereby measure an amount of urea remaining in mixed gas.

More specifically, a produced substance measuring mechanism is not the ammonia sensor 21, and the ammonia sensor 21 is replaced by a Fourier transform infrared spectroscopic analyzer 22. Further, a calculation part 5 is also configured to calculate a urea amount calculated value on the basis of a first isocyanic acid measured value measured at the first temperature by the produced substance measuring mechanism and a second isocyanic acid measured value measured at the second temperature by the produced substance measuring mechanism.

In other words, the calculation part 5 is one that, on the basis that in the case where urea is pyrolyzed, isocyanic acid is produced on a one-to-one basis on the basis of the above-described chemical formula 1, calculates a remaining urea amount, and calculates a molar number or the like of the remaining urea from a difference between the second isocyanic acid measured value and the first isocyanic acid measured value.

Even with such a configuration, the amount of the urea remaining in the exhaust gas can be measured.

Further, a third embodiment of the present invention is described. In the following description, members corresponding to those described in the first embodiment are denoted by the same signs.

Figure 4:
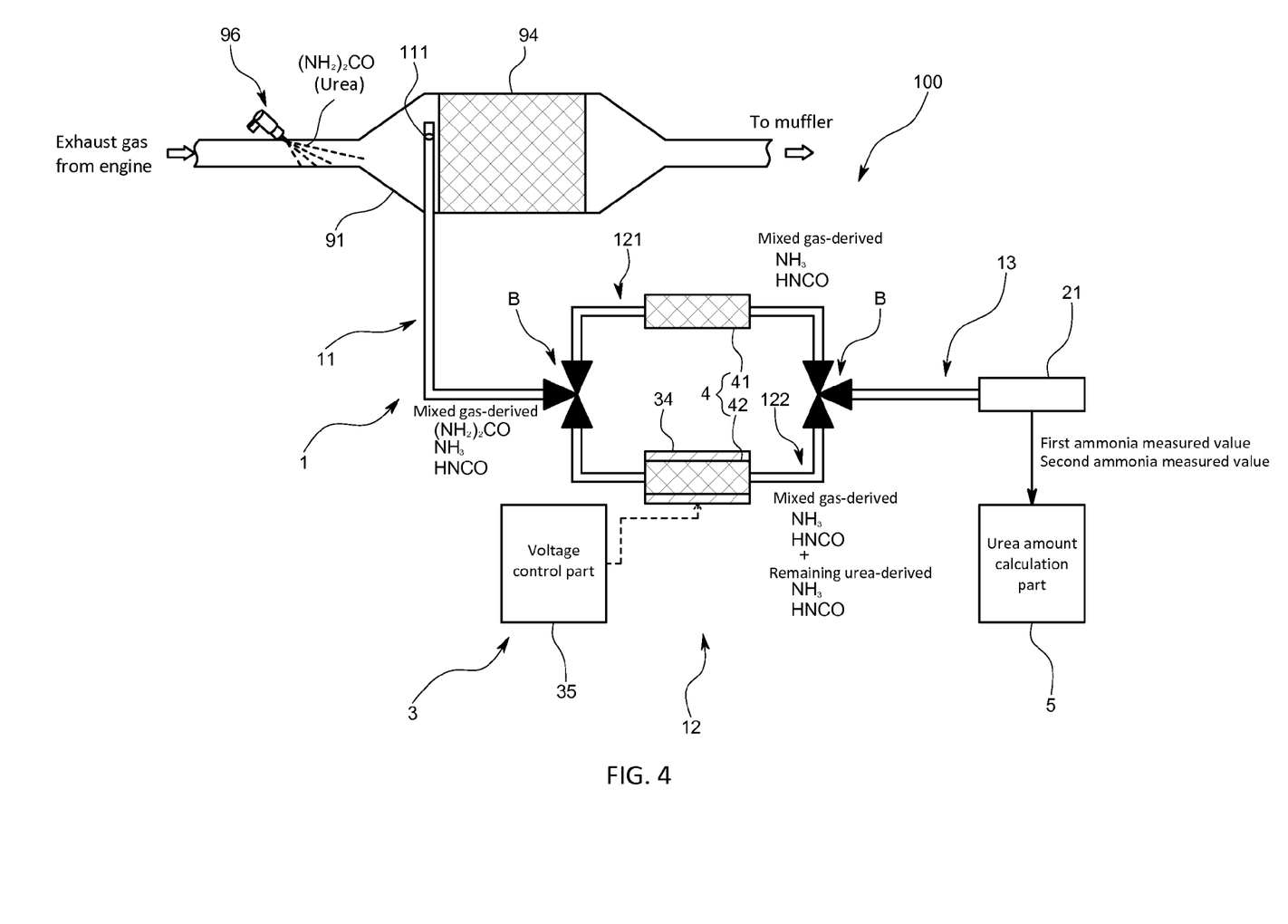
FIG. 4 is a schematic diagram illustrating a gas analysis apparatus according to a third embodiment of the present invention.

The decomposition reaction controlling mechanism 3 in the first embodiment is configured to establish the state where the pyrolysis of urea is prevented and the state where only the pyrolysis of urea is caused by regulating the temperatures of the first and second flow paths 121 and 122 with the first and second heaters 31 and 32; however, the third embodiment is adapted to calculate an amount of urea by electrolyzing urea into ammonia.

More specifically, as illustrated in FIG. 4, a second filter 42 is an electrically conductive one, and a decomposition reaction controlling mechanism 3 is configured to include: a power supply part 34 that applies AC voltage to the second filter 42; and a voltage control part 35 that controls the voltage applied by the power supply part 34. Also, inside a sampling pipe 1, temperature is kept less than the first temperature so as to prevent a decomposition reaction from being caused in remaining urea.

The gas analysis apparatus 100 of the third embodiment is adapted such that the power supply part 34 generates a discharge in the filter 42 to produce the ammonia from the urea. Also, the voltage control part 35 is configured to apply the voltage appropriate to produce the ammonia from the urea by the discharge generated by the power supply part 34.

Even with such a configuration, a calculation part 5 can calculate an amount of the urea remaining in exhaust gas from a difference between a second ammonia measured value measured in a state where an ammonia amount is increased by the discharge and a first ammonia measured value measured in a state where a decomposition reaction is not caused.

Still further, a fourth embodiment of the present invention is described. In the following description, members corresponding to those described in the first embodiment are denoted by the same signs.

Figure 5:
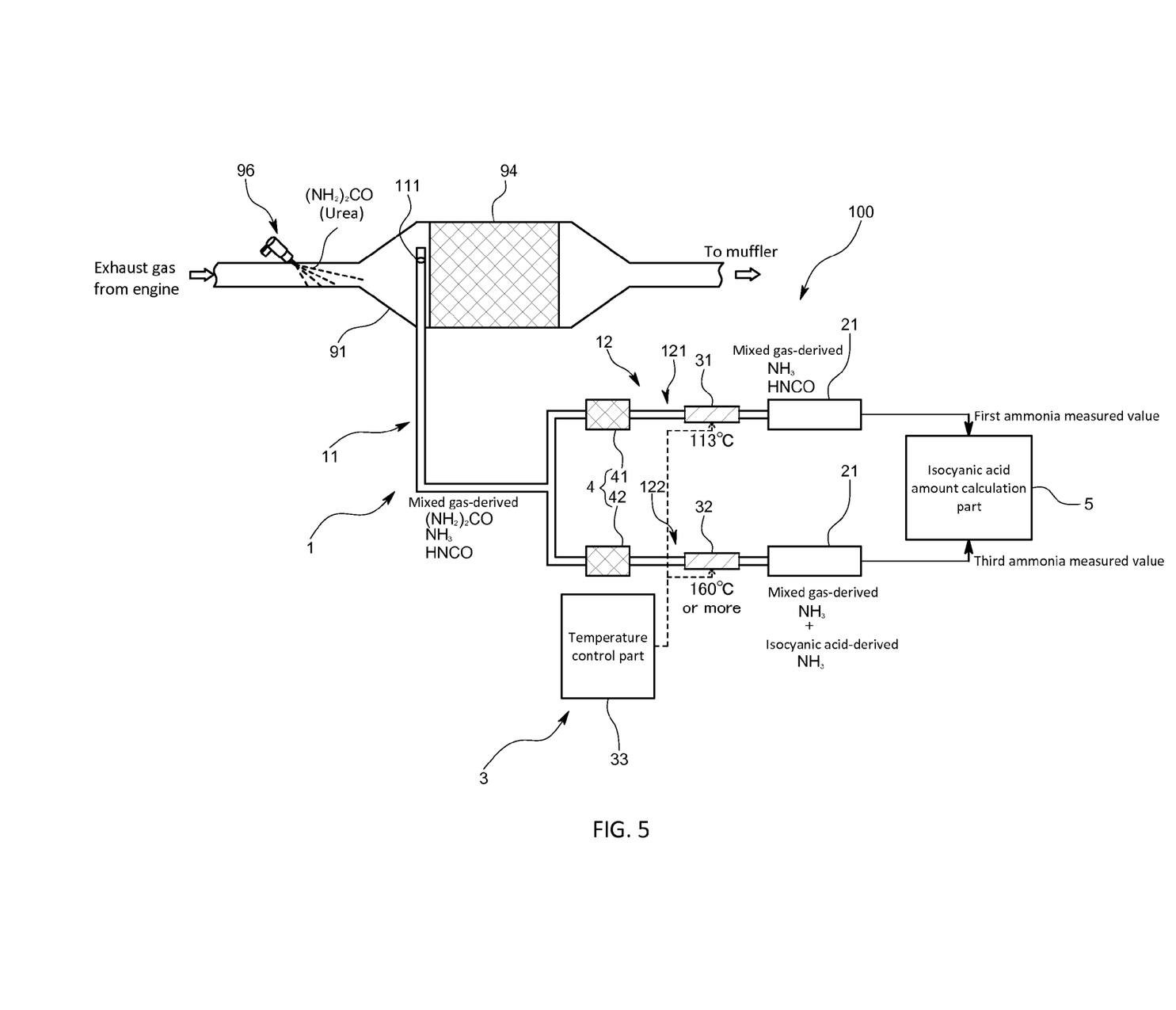
FIG. 5 is a schematic diagram illustrating a gas analysis apparatus according to a fourth embodiment of the present invention.

A gas analysis apparatus of the fourth embodiment is configured to calculate an amount of isocyanic acid contained in mixed gas by measuring ammonia. More specifically, as illustrated in FIG. 5, a mixed gas sampling pipe 1 branches halfway into two pipes to form a first flow path 121 and a second flow path 122, and the respective flow paths 121 and 122 are, sequentially from upstream sides, provided with: first and second filters 41 and 42 constituting a filter part 4; first and second heaters 31 and 32 constituting a decomposition reaction controlling mechanism 3; and ammonia sensors 21 provided at terminals thereof. That is, differently from the above-described first or second embodiment, the first and second heaters 31 and 32 are provided on a downstream side of the filter part 4 so as not to heat the filter part 4 itself, but to heat only mixed gas having passed through the filter part 4. Further, a calculation part 5 is, differently from those in the above-described first to third embodiments, configured to calculate not a urea amount but an isocyanic acid amount calculated value that is a value related to an amount of the isocyanic acid contained in the mixed gas.

In the following, described are a configuration and operation of a temperature control part 33 that controls the respective heaters 31 and 32, and those of the calculation part 5 in the fourth embodiment.

The temperature control part 33 is configured to use the first heater 31 to control temperature of the mixed gas having passed through the first filter 41 to a first temperature that is equal to or more than a temperature at which water is evaporated, and less than a pyrolysis starting temperature that is a temperature at which the production of ammonia and isocyanic acid is started by a pyrolysis reaction of urea. More specifically, the first temperature is set less than 133° C. Preferably, the first temperature is set equal to or more than 40° C. and less than 128° C. That is, in the case where the mixed gas flows through the first flow path 121, the present embodiment is adapted to, while preventing condensation, keep amounts of ammonia and isocyanic acid produced by the decomposition of urea from changing in an exhaust pipe 91, and also regulate the temperature so as to keep the temperature at 113° C. to prevent the isocyanic acid contained in the mixed gas from being decomposed.

Further, regarding the second flow path 122, the temperature control part 33 uses the second heater 32 to control temperature of the mixed gas having passed through the second filter 42 to a third temperature that is equal to or more than a hydrolysis starting temperature that is a temperature at which the production of ammonia is started by a hydrolysis reaction of isocyanic acid. More specifically, the third temperature is set to be equal to or more than 160° C. In the case of considering unevenness and deviation of temperature control, the third temperature is preferably set equal to or more than 165° C. In the fourth embodiment, the remaining urea is collected by the second filter 42, so that no urea is presented around the second heater 32 on the downstream side of the second filter 42, and therefore even in the case of heating at 160° C. or more, only the hydrolysis of the isocyanic aid is caused.

The calculation part 5 is configured to, on the basis of a first ammonia measured value that is ammonia concentration measured in a state where the mixed gas flowing through the first flow path 121 is kept at the first temperature, and a third ammonia measured value that is ammonia concentration measured in a state where the mixed gas flowing through the second flow path 122 is kept at the third temperature, calculate an isocyanic acid calculated value corresponding to an amount of the isocyanic acid produced by the decomposition of the urea in the exhaust pipe 91. More specifically, on the basis that, from the above-described chemical formula 2 that is a formula related to the hydrolysis of isocyanic acid, a difference between the third ammonia measured value and the first ammonia measured value corresponds to the amount of the isocyanic acid originally contained in the mixed gas, the calculation part 5 calculates the isocyanic acid amount calculated value. For example, the calculation part 5 is adapted to calculate a molar number of ammonia on the basis of the difference between the third ammonia measured value and the first ammonia measured value, and on the assumption that isocyanic acid having an equivalent molar number is contained in the mixed gas on the basis of the chemical formula 2, output the isocyanic acid amount calculated value.

As described, the gas analysis apparatus 100 of the fourth embodiment is adapted to, before starting to heat the mixed gas with the first and second heaters 31 and 32, collect the remaining urea with the first and second filters 41 and 42, and therefore at the time of the measurement, the amounts of ammonia and isocyanic acid can be prevented from being varied by new urea decomposition. Accordingly, only the ammonia originally contained in the mixed gas, and ammonia produced from the isocyanic acid by the hydrolysis can be measured, and therefore from the ammonia measured values, the calculation part 5 can accurately calculate the amount of the isocyanic acid contained in the mixed gas.

A variation of the fourth embodiment is described.

In the fourth embodiment, the calculation part 5 is configured to calculate the accurate amount of the isocyanic acid on the basis of the first ammonia measured value and the third ammonia measured value; however, for example, the calculation part 5 may be adapted to calculate whether or not isocyanic acid is contained in the mixed gas. Examples include one configured such that in the case where the difference between the third ammonia measured value and the first ammonia measured value is equal to or more than a predetermined value, the calculation part 5 determines that isocyanic acid is contained in the mixed gas, whereas in the case where the difference is substantially zero, the calculation part 5 determines that isocyanic acid is not contained in the mixed gas to the extent of being detected. Even with such a configuration, the presence or absence of isocyanic acid contained in the mixed gas, or whether or not the predetermined amount of isocyanic acid or more is contained can be accurately determined. Further, the presence or absence of solid urea contained in the mixed gas can also be determined in the same manner.

Other embodiments are described.

Each of the above-described embodiments is one that is provided with: the first flow path for making the ammonia or isocyanic acid originally contained in the exhaust gas arrive at the produced substance measuring mechanism without change; and the second flow path for making the mixed gas in which the remaining urea is decomposed arrive at the urea-derived substance measuring instrument; however, the present invention may be adapted to be able to measure two ammonia measured values or isocyanic acid measured values necessary to calculate the remaining urea amount by performing temperature control or the like to switch a reaction state in a common flow path.

Also, the calculation part calculates an amount of the urea remaining in the mixed gas on the assumption of an ideal state where ammonia or isocyanic acid is produced on the one-to-one basis with respect to urea; however, for example, the present invention may be adapted to make a correction in consideration of a reduction in yield due to the production of biuret or cyanuric acid. Specifically, it is only necessary that the present invention is adapted to, on the basis of a temperature condition set for the inside of the mixed gas sampling pipe, preliminarily measure a yield of ammonia or isocyanic acid, and on the basis of the yield, correct the urea amount. In the case of making the correction, the correction may be made on the basis of production ratios of ammonia in the chemical formulae 4 and 5. Also, the second temperature range may be set equal to or more than 133° C. and less than 188° C. in order to prevent the production of cyanuric acid to decrease a measurement error.

It is only necessary that a measured or calculated value of ammonia, isocyanic acid, or urea is a value related to quantity such as concentration, molar number, or flow rate.

As the produced substance measuring mechanism, a mechanism using a measuring instrument or measuring device other than the ammonia sensor using zirconium or FTIR is also possible. For example, ammonia and isocyanic acid may be measured with a laser. In short, any measuring mechanism is possible as long as a measured value is not significantly changed by the influence of a non-target substance.

Besides, it should be appreciated that unless contrary to the scope of the present invention, various modifications and combinations of the embodiments may be made.

INDUSTRIAL APPLICABILITY

As described, according to the gas analysis apparatus of the present invention, remaining urea that has been unmeasurable in the past because of passing through a produced substance measuring mechanism as a state of urea can also be accurately measured to accurately calculate a remaining urea amount. Accordingly, by applying the present invention, an exhaust gas analysis apparatus suitable to be used for research or the like of urea SCR or the like can be provided.

The invention claimed is:

1. A gas analysis apparatus comprising:
    a mixed gas sampling pipe that does not provide a flow path to a selective catalytic reduction (SCR) catalyst and that, from a sampling port formed on one end side inside an exhaust gas pipe, samples mixed gas that is a mixture of exhaust gas emitted from an internal combustion engine and a misty urea aqueous solution;
    a decomposition reaction controlling mechanism that controls a decomposition reaction of urea or isocyanic acid in the mixed gas sampling pipe;
    a produced substance measuring mechanism that is provided on an other end side of the mixed gas sampling pipe downstream from the decomposition reaction controlling mechanism and measures a value related to an amount of a substance produced from the urea or the isocyanic acid in the urea aqueous solution;
    a calculation part configured to calculate an amount of the urea contained in the mixed gas, on a basis of a measured value measured by the produced substance measuring mechanism; and
    a filter, including fibers, that is provided between the sampling port and the produced substance measuring mechanism in the mixed gas sampling pipe to collect the urea in a solid state or in a state of being dissolved in water in the mixed gas, wherein the decomposition reaction controlling mechanism is configured to control a temperature of the filter or a voltage applied to the filter.

2. The gas analysis apparatus according to claim 1, wherein:
    the produced substance measuring mechanism is configured to measure a value related to an amount of ammonia,
    the decomposition reaction controlling mechanism is configured to be able to control the temperature of the filter to a first temperature that is less than a pyrolysis starting temperature that is a temperature at which production of ammonia and isocyanic acid is started by a pyrolysis reaction of urea, or a second temperature that is equal to or more than the pyrolysis starting temperature and less than a hydrolysis starting temperature that is a temperature at which production of ammonia is started by a hydrolysis reaction of isocyanic acid, and the calculation part is configured to calculate the amount of the urea on a basis of a first ammonia measured value measured at the first temperature by the produced substance measuring mechanism and a second ammonia measured value measured at the second temperature by the produced substance measuring mechanism.

3. The gas analysis apparatus according to claim 2, wherein:
the produced substance measuring mechanism is configured to measure a value related to an amount of isocyanic acid,
the decomposition reaction controlling mechanism is configured to be able to control the temperature of the filter to a first temperature that is less than a pyrolysis starting temperature that is a temperature at which production of ammonia and isocyanic acid is started by a pyrolysis reaction of urea, or a second temperature that is equal to or more than the pyrolysis starting temperature and less than a hydrolysis starting temperature that is a temperature at which production of ammonia is started by a hydrolysis reaction of isocyanic acid, and
the calculation part is configured to calculate the amount of the urea on a basis of a first isocyanic acid measured value measured at the first temperature by the produced substance measuring mechanism and a second isocyanic acid measured value measured at the second temperature by the produced substance measuring mechanism.

4. The gas analysis apparatus according to claim 2, wherein the first temperature is less than 133° C., and the second temperature is equal to or more than 133° C. and less than 160° C.

5. A gas analysis apparatus comprising:
a mixed gas sampling pipe that that does not provide a flow path to a selective catalytic reduction (SCR) catalyst and that, from a sampling port formed on one end side inside an exhaust gas pipe, samples mixed gas that is a mixture of exhaust gas emitted from an internal combustion engine and a misty urea aqueous solution;
a decomposition reaction controlling mechanism that controls a decomposition reaction of urea or isocyanic acid in the mixed gas sampling pipe;
a produced substance measuring mechanism that is provided on an other end side of the mixed gas sampling pipe downstream from the decomposition reaction controlling mechanism and measures a value related to an amount of a substance produced from the urea or the isocyanic acid in the urea aqueous solution;
a calculation part configured to calculate an amount of the isocyanic acid contained in the mixed gas, on a basis of a measured value measured by the produced substance measuring mechanism; and
a filter, including fibers, that is provided between the sampling port and the produced substance measuring mechanism in the mixed gas sampling pipe to collect the urea in a solid state or in a state of being dissolved in water in the mixed gas, wherein the decomposition reaction controlling mechanism is configured to control a temperature of an inside of the mixed gas sampling pipe on the downstream side of the filter.

6. The gas analysis apparatus according to claim 5, wherein:
the produced substance measuring mechanism is configured to measure a value related to an amount of ammonia,
the decomposition reaction controlling mechanism is configured to be able to control the temperature of the inside of the mixed gas sampling pipe on the downstream side of the filter to a first temperature that is less than a pyrolysis starting temperature that is a temperature at which production of ammonia and isocyanic acid is started by a pyrolysis reaction of urea, or a third temperature that is equal to or more than a hydrolysis starting temperature that is a temperature at which production of ammonia is started by a hydrolysis reaction of isocyanic acid, and
the calculation part is configured to calculate the amount of the isocyanic acid on a basis of a first ammonia measured value measured at the first temperature by the produced substance measuring mechanism and a third ammonia measured value measured at the third temperature by the produced substance measuring mechanism.

7. The gas analysis apparatus according to claim 6, wherein the first temperature is less than 133° C., and the third temperature is equal to or more than 160° C.

* * * * *